United States Patent
Pauker

(10) Patent No.: US 6,503,194 B2
(45) Date of Patent: Jan. 7, 2003

(54) ENDOSCOPE SHAFT COMPRISING A MOVABLE DISTAL END

(76) Inventor: Fritz Pauker, Weiherbeiten 8, D-86316 Friedberg (DE)

( * ) Notice: Subject to any disclaimer, the term of this patent is extended or adjusted under 35 U.S.C. 154(b) by 0 days.

(21) Appl. No.: 09/801,570

(22) Filed: Mar. 7, 2001

(65) Prior Publication Data

US 2001/0053874 A1 Dec. 20, 2001

Related U.S. Application Data

(63) Continuation-in-part of application No. 09/305,850, filed on May 5, 1999, now Pat. No. 6,358,199, which is a continuation-in-part of application No. 09/095,857, filed on Jun. 11, 1998, now Pat. No. 6,286,555.

(51) Int. Cl.$^7$ .............................................. A61B 1/01
(52) U.S. Cl. ...................... 600/152; 600/146; 901/22
(58) Field of Search ................................ 600/130–192, 600/144, 145, 152, 151; 604/95.01, 95.03; 901/22

(56) References Cited

U.S. PATENT DOCUMENTS

| | | | | |
|---|---|---|---|---|
| 4,661,039 A | * | 4/1987 | Brenholt | 414/735 |
| 4,976,191 A | * | 12/1990 | Suzumori et al. | 92/103 R |
| 5,179,934 A | * | 1/1993 | Nagayoshi et al. | 600/152 |
| 5,469,756 A | * | 11/1995 | Feiten | 74/490.05 |

* cited by examiner

Primary Examiner—John Mulcahy
(74) Attorney, Agent, or Firm—Graybeal Jackson Haley LLP

(57) ABSTRACT

The invention relates to an endoscope shaft comprising a movable distal end portion and an operating device which is operatively connected through the endoscope shaft with the distal end portion for the operation thereof. The distal end portion comprises a plurality of longitudinally stacked swelling bodies, two of which at a time are located diametrically with respect to each other and form a layer and two longitudinally directly adjacent pairs of bodies of which at a time are phase-shifted by 90°.

8 Claims, 2 Drawing Sheets

ENDOSCOPE SHAFT COMPRISING A MOVABLE DISTAL END

This is a Continuation-In-Part of U.S. application Ser. No. 09/095,857 files on Jun. 11, 1998, now U.S. Pat. No. 6,286,555, and U.S. application Ser. No. 09/305,850 files on May 5, 1999, now U.S. Pat. No. 6,358,199.

DESCRIPTION

The present invention relates to an endoscope shaft in accordance with the preamble of claim 1.

Endoscopes are instruments especially for exploring hollows or tube-shaped conduits of the body, especially for medical purposes. Especially endoscopes for exploring the esophagus, the stomach, the duodenum from the stomach, the intestine from the anus, the urethra, the vesica and the ureter have become known. Such an endoscope is equipped with a lighting device at its front end and with an optical system for visually detecting the area located in front of the body hollow or body canal to be explored. While until recently the optical information detected in front of the front end of the endoscope has been usually transmitted by means of fiber optics through the endoscope towards its operating end behind, the insertion of a camera chip at the front end of the endoscope as well as the electric image transmission and the illustration of the obtained optical information on a monitor constitutes the latest prior art now.

Furthermore, endoscopes usually comprise a so-called working conduit through which various working instruments can be introduced and operated. For example, small-forceps for taking tissue specimens, biopsy needles, heated cutting wires, small scissors, coagulation electrodes or the like are introduced so as to perform surgical measures at the affected tissue, if need be. Finally, as a rule, a fluid conduit for wash and operating wires for bending the front end of the endoscope in various directions are provided. These operating wires are guided through individual conduits within the endoscope shaft towards the front or distal end thereof so as to bend it three-dimensionally by up to 160° in the opposite direction of the endoscope shaft.

In this connection essential problems arise now, especially with respect to the tactical feeling which is given to the operator during the bending process. Therefore, there is the danger that, when the intestine is explored, the intestine wall is injured during the bending process of the distal end. Furthermore, it must be possible to be able to exactly position the distal end in the area to be explored and to be treated, if necessary, which requires a sufficient flexibility as well as at the same time a sufficient stiffness, after the predetermined bending position had been reached.

In view of these problems, it is the object of the invention to provide a construction for a distal end portion of an endoscope shaft, said construction ensuring a sufficient flexibility as well as a sufficient stiffness, when the predetermined bending position has been reached, and furthermore giving a sufficient tactical feeling to the operator. According to the present invention, this object is achieved by an endoscope shaft comprising the features of the enclosed claim 1.

Accordingly, the invention consists in forming the distal end portion of a plurality of bellow-shaped bodies or swelling bodies longitudinally juxtaposed and/or stacked, two of which at a time are located diametrically with respect to each other and form a body layer and two longitudinally directly adjacent pairs of bodies of which at a time are phase-shifter by 90°. Hereby a construction is obtained in which the individual swelling bodies seen in the longitudinal direction are alternately arranged at twelve and six o'clock according to the one layer and at three and nine o'clock according to the neighboring layer. In this way it is possible to achieve a bend-off of the distal end into the intended direction by correspondingly operating the bellows having the same angular position, when they are swelling or contracting, wherein, when the predetermined angular position of the distal end has been reached, the swelling bodies are virtually frozen in this position and thus the fixing of the distal end is maintained.

It has turned out to be particularly advantageous to form the swelling bodies as hydraulically or pneumatically operable bellows according to subclaim 3, whereby a simple and less expensive mode of operation is rendered possible, for instance, by a correspondingly formed pressure medium source, for instance, in the shape of a hand pump giving a sufficient tactical feeling to the operator.

Further advantageous embodiments of the invention are the subject matter of the other subclaims.

Hereinafter the invention will be explained in detail by way of a preferred embodiment with reference to the accompanying figures, in which FIG. 1 shows a schematic representation of a distal end portion of an endoscope shaft in accordance with a preferred embodiment of the invention in a cross-sectional view.

Figure 1:
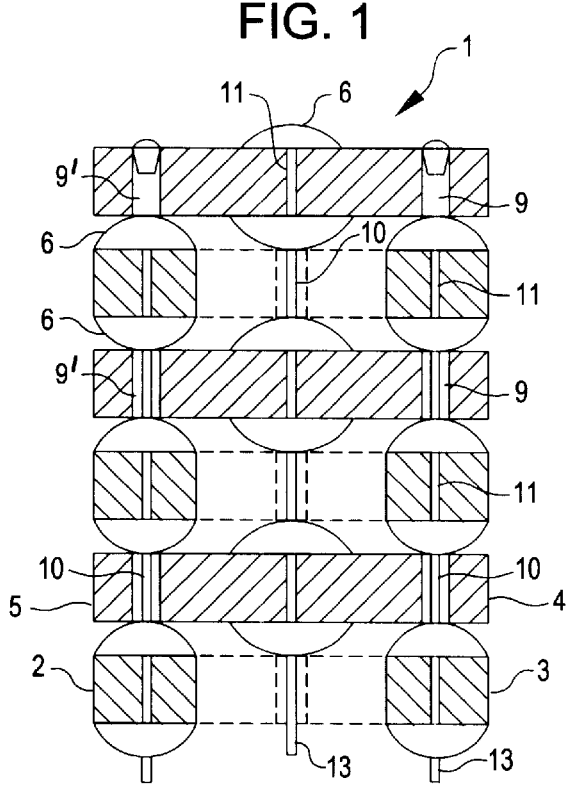

In FIG. 1 the movable distal end portion of an endoscope shaft according to the preferred embodiment of the invention is shown as schematic drawing.

As can be taken from FIG. 1, the movable distal end portion 1 of the endoscope shaft according to the invention comprises a plurality of bodies 2, 3, 4 longitudinally juxtaposed or stacked, each layer being formed of two bodies arranged diametrically with respect to each other.

Figure 2:
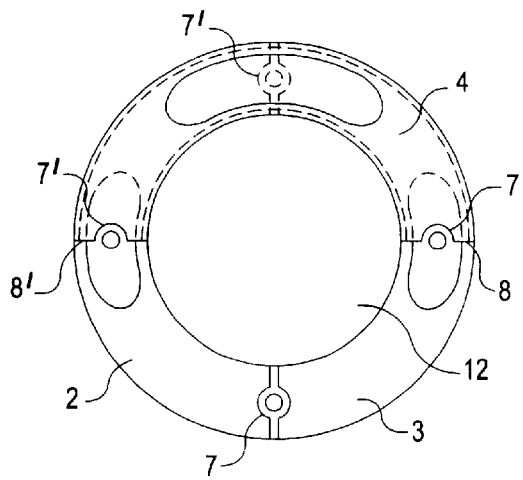
FIG. 2 shows a top view of the distal end portion as schematic representation.
Figure 3A:
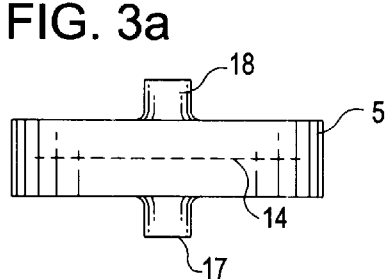
FIGS. 3a to 3d show the structure of a swelling body.
Figure 3C:
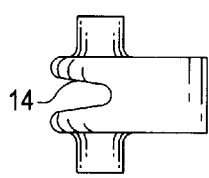
Figure 3B:
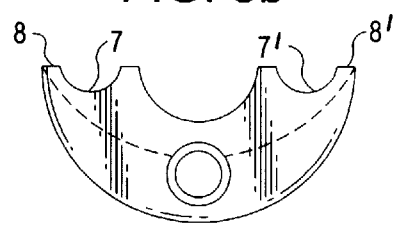
Figure 3D:
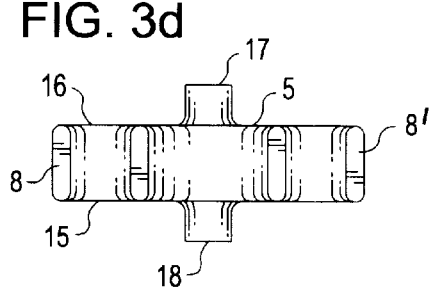

FIG. 2 shows a top view of the movable distal end portion 1 as a schematic representation. Accordingly, each body 2, 3, 4 consists of a semicircular disc-like ring element 5 forming swelling bodies 6 in its central portion seen in the circumferential direction. At the two respective end faces of the semicircular ring disc 5 notches 7, 7' extending in the direction of thickness of the disc 5 are formed preferably in semicircular shape. The semicircular ring discs 5 are arranged adjacent to each other in each layer at the two end faces 8, 8' thereof such that the opposed notches 7,7; 7', 7' define two diametrically opposed through holes 9, 9' at the respective end faces.

As can be further taken from FIG. 1, the pairs of bodies which are directly adjacent in the longitudinal direction of the distal end portion are additionally phase-shifter by 90°. Hereby the swelling bodies 6 are alternately arranged at twelve and six o'clock with respect to the one layer and at three and nine o'clock on the respectively neighboring layer.

According to the present embodiment, the swelling bodies 6 are formed as extendable bellows which can be operated pneumatically or hydraulically. As an alternative thereof it is also possible, of course, to form the swelling bodies 6 as piezoelectric elements.

The swelling bodies 6, in the present case the expandable bellows, form a swivel and/or bend-off mechanism of the movable distal end. To this end, all bellows having the same angular position, i.e. the bellows in the twelve o'clock position, in the three o'clock position, in the six o'clock position and in the nine o'clock position are coupled with each other. This coupling consists of a piece of duct 10 which connects two longitudinally spaced bellows having the same angular position both mechanically and hydraulically and/or pneumatically, these pieces of ducts 10 extending through the through holes 9, 9' of the pair of bodies mounted therebetween. Consequently, a hydraulic and/or pneumatic fluid communication as well as a mechanical coupling is produced by the pieces of ducts 10 for preventing the individual layers from falling apart.

According to FIG. 1, the bellows are principally provided at the opposite flat sides of the semicircular ring discs 5 and have a fluid connection with each other by through bores 11 through which the ring discs 5 are extending.

As can be seen from FIG. 2, for each layer a central through hole 12 extending along the entire movable distal end portion 1 and forming a working conduit for introducing surgical instruments, auxiliary instruments or optical equipment is formed by juxtaposing the semicircular ring discs 5 according to the invention.

The function principle of the movable distal end portion according to the invention can be summarized as follows:

If a pressure medium, for instance a hydraulic fluid, is pumped into the fluid-coupled bellows through the pieces of ducts 10 in a selected angular position, this causes the bellows to widen substantially in a longitudinal direction of the distal end portion 1, whereby the semicircular ring discs 5 are spaced apart from each other in the area of this angular position. As no pressure is applied to and/or the pressure is even relieved from all further bellows in the respective other angular positions, this causes each layer consisting of two ring discs 5 to tip, whereby the distal end portion is gradually bending over the entire longitudinal extension thereof. The more hydraulic fluid is pressed into just pressurized the bellows, the larger becomes the degree of curvature of the end portion so far that a bendoff of almost 160° can be attained.

Such a bending motion in a direction of movement can be super-imposed, of course, by pressurizing bellows in a different angular position, for instance in an angular position offset by 90° hereto, whereby a kind of tumbling motion of the distal end portion is resulting. It is also possible to apply pressure or to relieve pressure from all bellows in all angular positions so as to longitudinally displace or contract the distal end portion in the area of total possible expansion of all bellows longitudinally spaced apart from each other.

As soon as the distal end of the movable end portion has adopted a particular bending position, the pressurization of the respective bellows of one or plural angular positions is stopped, whereby the distal end portion is fixedly maintained in this bending position due to the incompressible property of the hydraulic fluid.

This fixing is dependent on the elasticity in a radial direction of the bellows themselves, wherein concerning the design of each semicircular ring disc a good elasticity in the longitudinal direction but an as stiff configuration as possible in the radial direction is strived for, as it will be described hereinafter by way of a concrete design.

As can be further taken from FIG. 1, the semicircular ring discs 5 of the bottom layer according to FIG. 1 include connecting sleeves 13 for connecting a hydraulic pipe system. This hydraulic pipe system not shown in the present Figures substantially comprises four conduits which are guided through the endoscope shaft, which is not shown either, in working conduits formed therein and are connected to a central hydraulic pressure source. As a hydraulic pressure source preferably a manually operable pressure pump is suited which consists of four individual pumps which are operable independently of each other or coupled in such a manner that, when pressure is applied to the bellows of one angular position, the pressure is relieved in the bellows of the opposed angular position. Due to such a reciprocal relation between the application of pressure and a pressure relief in respectively opposed rows of bellows, the mobility of the distal end portion can be further increased and the positioning capability can be improved.

The latter even permits the exploration, e.g., of the intestine wall in the area of the sphincter muscle from the side of the intestine.

In FIGS. 3a to 3d the design of a semicircular ring disc 5 is shown in great detail. As can be taken therefrom, the ring disc 5 consists of a synthetic body having a predetermined thickness which forms a hollow space The wall of the body is inwardly folded at least once at the radially outer side so as to form a bellow 14.

At the mutually opposing side faces 15, 16 of the ring disc 5 connecting sleeves 17, 18 are formed which are arranged in alignment and open into the hollow of the ring body 5. The connecting sleeves 17, 18 can be formed integrally with the ring disc 5 or can be welded thereto. The ring body 5 preferably consists of two halves of a shell which are welded to each other along the radially outer side and the radially inner side in a circumferential direction.

Semicircular notches 7, 7' are formed at the two end faces 8, 8' of the semicircular ring disc 5 in the direction of thickness of the ring disc 5.

Figure 4:
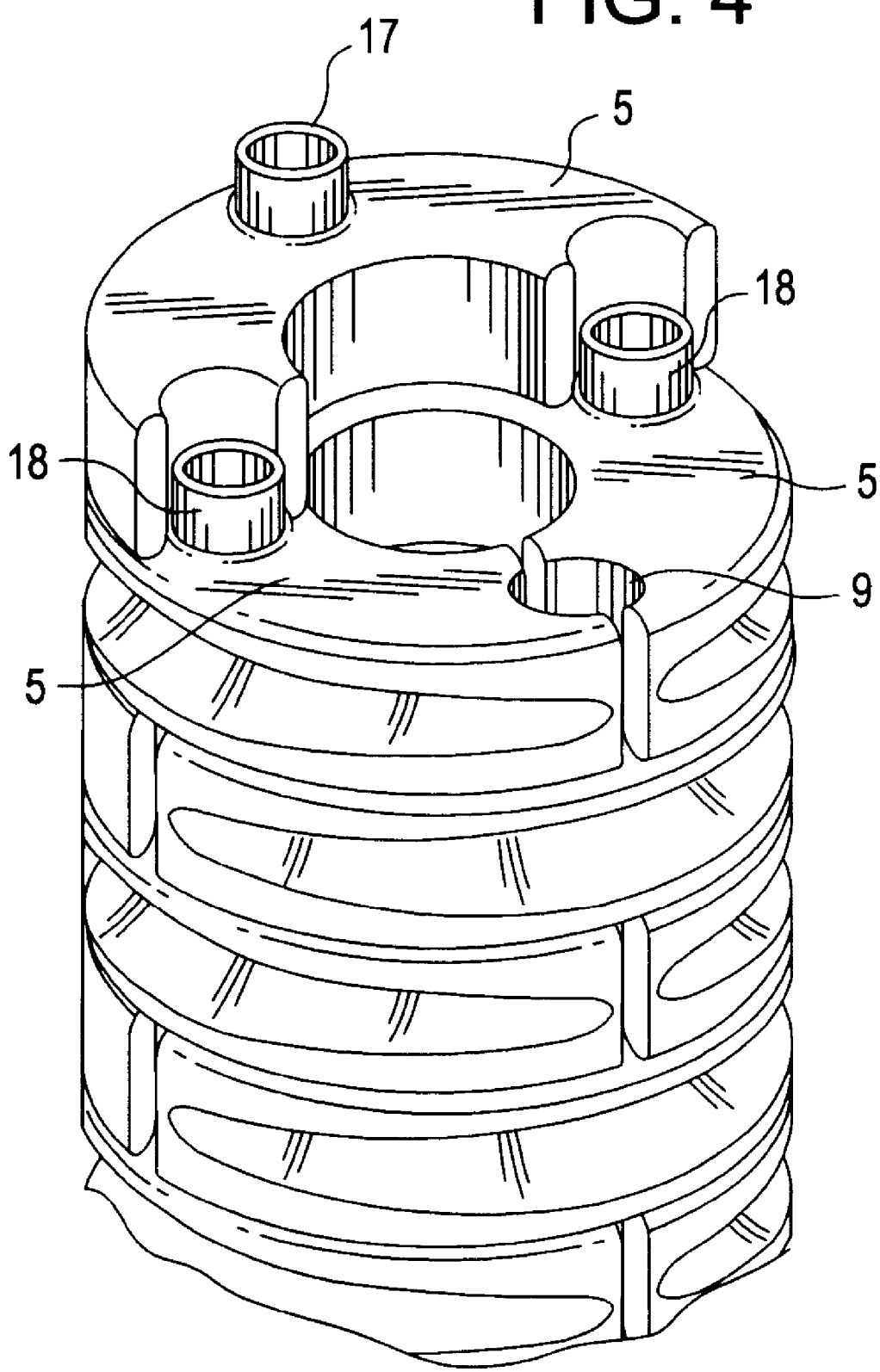
FIG. 4 shows the combination of a plurality of swelling bodies in a perspective view forming the distal end in accordance with the preferred embodiment.

In FIG. 4 the movable distal end portion is structurally shown.

As can be seen therefrom, two of the above-described ring discs 5 at a time juxtaposed at their respective end faces 8, 8' form a layer, wherein the pairs of ring discs of each layer which are arranged directly adjacent to each other are phase-shifted by 90°. In order to fix the ring discs 5 which are located at an angular position seen in the longitudinal direction, the connecting sleeves 17, 18 extending through the through holes 9, 9' which are formed in the one layer by the notches 7, 7' formed at the end face are glued or welded to each other. Hereby the above-mentioned piece of duct 10 as well as the mechanical connection of the coupled ring discs 5 in longitudinal direction are brought about.

Alternatively to the above-mentioned synthetic material design, also rubber or rubber laminate can, of course, be the material to be used for the distal end portion 1. The distal end portion is welded onto the end front face of the endoscope shaft such that in the two bottom layers the free connecting sleeves 13 make a fluid connection with the hydraulic conduits along the hydraulic shaft.

The invention relates to an endoscope shaft comprising a movable distal end portion and an operating device which is operatively connected through the endoscope shaft with the distal end portion for the operation thereof. The distal end portion comprises a plurality of longitudinally stacked swelling bodies, two of which at a time are located diametrically with respect to each other and form a layer and two longitudinally directly adjacent pairs of bodies of which at a time are phase-shifted by 90°.

What is claimed is:

1. An endoscope shaft comprising:
   a movable distal end portion comprising a plurality of longitudinally stacked semicircular disc-like ring elements each including a swelling body wherein two of said ring elements form a layer with their respective swelling bodies located diametrically opposite each other, and wherein the swelling bodies in each layer of ring elements are phase-shifted 90 degrees relative to the swelling bodies of a longitudinally adjacent layer of ring elements.

2. An endoscope shaft according to claim 1, wherein all swelling bodies located at twelve, at three, at six and at nine o'clock each are longitudinally coupled with each other.

3. An endoscope shaft according to claim 2, wherein said swelling bodies are hydraulically or pneumatically operable bellows.

4. An endoscope shaft according to claim 3, wherein the coupling is both mechanical and hydraulic and/or pneumatic coupling, and wherein at least a piece of duct is provided between two bellows at a time which are coupled to each other and are longitudinally spaced apart, said piece of duct being fixedly mounted to said bellows.

5. An endoscope shaft according to claim 4, wherein the swelling bodies of each layer interact to form a central through hole.

6. An endoscope shaft according to claim 5, wherein said swelling body forms a hollow and is folded at its radial outside.

7. An endoscope shaft according to claim 6, wherein said swelling body is provided at its two front faces with connecting sleeves opening into the hollow and being connected with connecting sleeves of the respective longitudinally spaced swelling bodies at an equal angular position while forming said piece of duct.

8. An endoscope shaft according to claim 7, wherein said swelling body has at its end faces longitudinally extending notches which, upon the formation of a layer, form two diametrically opposite through conduits through each of which a piece of conduit is guided.

* * * * *